(12) United States Patent
Hong et al.

(10) Patent No.: US 8,580,818 B2
(45) Date of Patent: Nov. 12, 2013

(54) COMBINATION DRUG CONTAINING PROBUCOL AND A TETRAZOLYLALKOXY-DI HYDROCARBOSTYRIL DERIVATIVE WITH SUPEROXIDE SUPRESSANT EFFECTS

(75) Inventors: Ki Whan Hong, Busan (KR); Tomohiro Yoshikawa, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 350 days.

(21) Appl. No.: 12/065,619

(22) PCT Filed: Sep. 14, 2006

(86) PCT No.: PCT/JP2006/318675
§ 371 (c)(1),
(2), (4) Date: Mar. 11, 2009

(87) PCT Pub. No.: WO2007/032557
PCT Pub. Date: Mar. 22, 2007

(65) Prior Publication Data
US 2009/0176826 A1    Jul. 9, 2009

Related U.S. Application Data

(60) Provisional application No. 60/716,954, filed on Sep. 15, 2005, provisional application No. 60/761,775, filed on Jan. 25, 2006.

(51) Int. Cl.
*A01N 43/12* (2006.01)
*A61K 31/445* (2006.01)
(52) U.S. Cl.
USPC .................................................. 514/312
(58) Field of Classification Search
USPC ........................................................ 514/312
See application file for complete search history.

(56) References Cited

U.S. PATENT DOCUMENTS

| 4,277,479 | A | 7/1981 | Nishi et al. |
| 6,218,403 | B1 | 4/2001 | Daste et al. |
| 6,235,311 | B1 | 5/2001 | Ullah et al. |
| 6,245,797 | B1 | 6/2001 | Winokur |
| 6,576,256 | B2 | 6/2003 | Liang et al. |
| 6,743,806 | B2 * | 6/2004 | Hong ............................ 514/312 |
| 2002/0115728 | A1 | 8/2002 | Stocker |
| 2003/0069221 | A1* | 4/2003 | Kosoglou et al. ........ 514/210.02 |
| 2004/0082608 | A1 | 4/2004 | Hong |
| 2005/0119272 | A1 | 6/2005 | Lautt et al. |

FOREIGN PATENT DOCUMENTS

| EP | 1 894 576 A1 | 5/2008 |
| JP | 4-193836 | 7/1992 |
| JP | 10-007590 | 1/1998 |
| JP | 2003-192573 A | 7/2003 |
| JP | 2005-232059 A | 9/2005 |
| WO | WO 98/11896 | 3/1998 |
| WO | WO 99/24400 | 5/1999 |
| WO | WO 00/21507 | 4/2000 |
| WO | WO 01/76632 A1 | 10/2001 |
| WO | WO 2006/132091 A1 | 12/2006 |

OTHER PUBLICATIONS

Araki et al (Chem. Pharm. Bull 49(8) 943-947 (2001).*
Bridges (Atherosclerosis (1991) 89(2-3):263-265 (Abstract).*
Lee et al. (J. Pharmacology and Experimental Therapeutics 313(2);502-509 (May 2005)).*
Kim et al. (Korean Cir. J (2000) 30(7); 811-818) (Abstract).*
Brandes Cir. Res. 2003:92; 583-585.*
M. Sekiya et al., "Effects of probucol and cilostazol alone and in combination on frequency of poststenting restenosis," American Journal of Cardiology, vol. 82, No. 2, 1998, pp. 144-147.
Yoshinori Shiraishi et al., "A study about the prophylactic effect of in-stent restenosis in coronary artery with probucol and cilostazol—A comparison with the administration group of ticlopidine-," Japanese Circulation Journal, vol. 64, Suppl. I, 2000, p. 567 (P434).
Yukihiko Abe et al., "Multidrug Hybrid Therapy including an Angiotensin Receptor Antagonist to Prevent Restenosis after Coronary Stenting (Preliminary Report)," Jpn J. Interv. Cardiol 2002, 17:259:262.
Yuetsu Ihara et al., "A family of familial hypercholesterolemia with cerebral infarction and without coronary heart disease"; "An unusual case with corneal opacity, polyneuropathy and carpal tunnel syndrome in the family: therapy with probucol and tocopherol nicotinate," Journal of the Neurological Sciences, 106 (1991) 10-18.
Tomomi Kimura et al., Nippon Rinsho, vol. 59, Suppl. 2 (2001), pp. 685-689.
Kon-nichi no Chiryoyaku (Current Drugs) (2003) published by Nankodo Co., Ltd. 2003, pp. 464, 465.

(Continued)

*Primary Examiner* — Shirley V Gembeh
(74) *Attorney, Agent, or Firm* — Finnegan, Henderson, Farabow, Garrett & Dunner, L.L.P.

(57) ABSTRACT

This invention relates to a combination drug comprising a combination of a tetrazolylalkoxy-dihydrocarbostyril derivative of the formula:

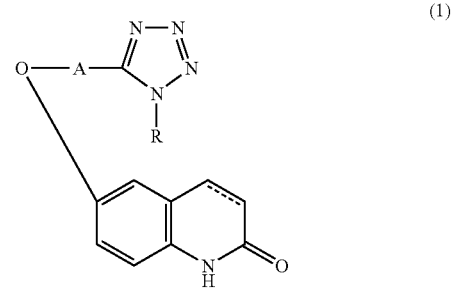

(1)

wherein R is cycloalkyl, A is lower alkylene, and the bond between 3- and 4-positions of carbostyril nucleus is single bond or double bond, or a salt thereof and Probucol, which is useful for preventing and treating cerebral infarction including acute cerebral infarction and chronic cerebral infarction, arteriosclerosis, renal diseases (e.g. diabetic nephropathy, renal failure, nephritis), and diabetes owing to synergistic superoxide suppressant effects of the combination.

1 Claim, 6 Drawing Sheets

(56) References Cited

OTHER PUBLICATIONS

Kon-nichi no Chiryoyaku (Current Drugs) (2003) published by Nankodo Co., Ltd. 2003, pp. 320, 322.
Journal of Blood Pressure (2003) vol. 10, No. 10, 1135-9.
Takei, K. et al., "Role of Cyclic Adenosine Monophosphate in Reducing Superoxide Anion Generation in Guinea Pig Alveolar Macrophages," Pharmacology, 1998, vol. 57, No. 1, pp. 1-7.
Mitsuhashi, Naomi et al., "Effect of Cilostazol, a Phosphodiesterase Inhibitor, on Carotid IMT in Japanese Type 2 Diabetic Patients," Endocrine Journal, 2004, vol. 51, No. 6, pp. 545-550.
Sasaki, Hidehisa et al., "Effects of Rifampicin on Hypolipidemic Action of Probucol," J. Japan Diab. Soc. 47(2): 103-109, 2004.
Office Action for counterpart JP Application No. 2008-514987 dated Feb. 14, 2012.
Office Action for counterpart JP Application No. 2008-514987 dated Jun. 12, 2012.
Maritm, A.C., et al., "Diabetes, Oxidative Stress, and Antioxidants: A Review," J. Biochem Molecular Toxicoloy, vol. 17, No. 1 (2003), pp. 24-38.
Tohma, Takeshi et al., "Cilostazol, a Phosphodiesterase Inhibitor, Reduces Microalbuminuria in the Insulin-Resistant Otsuka Long-Evans Tokushima Fatty Rat," Metabolism, vol. 53, No. 11 (2004), pp, 1405-1410.
Office Action for KR Application No. 10-2008-7008859 dated Nov. 14, 2012.

* cited by examiner

* $P < 0.05$;  $P < 0.01$; * $P < 0.001$ vs. vehicle ; # $P < 0.05$; ## $P < 0.01$ vs. probucol (30 mg/kg) group.

COMBINATION DRUG CONTAINING PROBUCOL AND A TETRAZOLYLALKOXY-DI HYDROCARBOSTYRIL DERIVATIVE WITH SUPEROXIDE SUPRESSANT EFFECTS

TECHNICAL FIELD

This invention relates to a combination drug for treating and preventing cerebral infarction, arteriosclerosis, renal diseases, or diabetes. More particularly, it relates to a combination drug for treating and preventing cerebral infarction, arteriosclerosis, renal diseases, or diabetes which comprises a combination of at least one of tetrazolylalkoxy-dihydrocarbostyril derivatives of the formula:

wherein R is a cycloalkyl group, A is a lower alkylene group, and the bond between 3- and 4-positions of the carbostyril nucleus means a single bond or a double bond, or a salt thereof and Probucol.

The combination drug of the present invention is effective on the cerebral infarction, arteriosclerosis, renal diseases, or diabetes owing to the superoxide suppressing activity based on the synergistic effects by combination of the above tetrazolylalkoxy-dihydrocarbostyril derivative (1) and Probucol (=4,4'-isopropylidenedithiobis[2,6-di-tert-butylphenol].

TECHNICAL BACKGROUND

Cerebral infarction including acute cerebral infarction and chronic cerebral infarction, also known as cerebrovascular accident or also as cerebromalacia, is caused by interruption of the blood supply to a part of the brain due to occlusion or coarctation of cerebral artery and/or vein to result in necrosis of the brain tissue or cells. The most important risk factors thereof are hypertension, heart disease, diabetes, and cigarette smoking. For remedy of the cerebral infarction, it is important to inhibit the development of necrosis due to free radical and cerebral expansion, and anticoaggulants, thrombolytic agents, such as urokinase, tissue plasminogen activator (tPA) have been used.

Arteriosclerosis, which term is often used interchangeably with atherosclerosis, is in the conditions that the walls of the arteries become thick and stiff and the blood flow to organs and tissues are restricted. Although the cause is unknown, it is suspected that it starts with damage or injury to the inner layer of an artery, and the damage may be caused by various factors, including high blood pressure, high cholesterol, an irritant (e.g. nicotine) and certain diseases such as diabetes. For the remedy of arteriosclerosis, various drugs have been used, for example, anticholesterol agents (e.g. probucol, statins, clofibrates), anti-platelet agents (e.g. aspirin), anticoagulant agents (e.g. heparin, warfarin), blood pressure controlling agents (e.g. angiotensin-converting enzyme (ACE) inhibitors, calcium channel blockers).

Renal diseases, including diabetic nephropathy, renal failure, and nephritis, are characteristic in the functional changes such as excess glomerular filtration and albuminuria and the histological changes such as glomerular sclerosis due to increase of extracellular matrix protein. It is considered that the renal diseases are caused by sustained high blood sugar, intracellular abnormal metabolism (e.g. increase of polyol pathway and hexosamine pathway, and activation of protein kinase C (PKC)) due to hyperglycemia, accumulation of advanced glycation end-products (AGE), pressure overload due to glomerular hypertension, or increased oxidant stress, and that the most important geneses of renal diseases are increased oxidant stress as well as hyperglycemia in the light of reports that active oxygen increases in the intracellular abnormal metabolism or in the process of formation of AGE (cf. Nature, 414, pp. 813-820, 2001) and that all of the increase of hexosamine pathway, the PKC activation and increase of AGEs are inhibited by inhibition of excess production of superoxide in mitochondria (cf. Nature, 404, pp. 787-790, 2000).

It is known that exacerbation of insulin resistance is important factor of diabetes onset, but the exacerbation of insulin resistance becomes not only pathogenesis of metabolic syndrome such as diabetes but also promotes the onset and development of cardiovascular diseases and renal diseases (cf. Arterioscler. Thromb. Vasc. Biol., 24, pp. 816-823, 2004), and hence, it has been considered that improvement of insulin resistance is useful for treating diabetes and diabetic complication. It is also reported that increased oxidant stress may be an important factor of inducing insulin resistance (cf. Nature, 440, pp. 944-948, 2006) and hence an oxidant stress inhibitor may be useful for the prevention and treatment of diabetes and of onset and development of renal diseases in the light of the improving activity of insulin resistance.

Although the population of diabetic patients with renal disease is increasing year by year, there has never been found a suitable therapy for treating renal diseases.

By the way, it has been known that oxygen is essential for a living body in order to maintain life, for example, to keep normal energy production and metabolism. Oxygen may be changed into so-called active oxygen in the living body. The active oxygen includes radical oxygen and non-radical oxygen. Among the active oxygen in a broad sense including lipid-related materials, the former radical oxygen includes a hydroxyl radical (.OH), an alkoxy radical, a peroxy radical, a hydroperoxy radical, a nitrogen monoxide, a nitrogen dioxide, superoxide ($O_2.^-$), etc. The latter non-radical oxygen group includes a singlet oxygen, ozone, hydrogen peroxide ($H_2O_2$), a lipid hydroperoxide, etc.

As an active oxygen which may be affective on tissue cells, there are radical oxygens of $O_2.^-$ and .OH, and non-radical oxygen of $H_2O_2$ (cf. YAKUGAKU ZASSHI 122(3), pp. 203-218 (2002)). The $O_2.^-$ produces oxygen and hydrogen peroxide by the action of superoxide dismutase (SOD) in the living body. Hydrogen peroxide is changed into .OH by catalytic action of iron ion, cupper ion included in cells. The hydroxyl radical attacks directly DNA, proteins in the living body. On the other hand, the hydroxyl radical reacts with lipids and thereby is converted into lipid radical and then produce lipid hydroperoxide.

Thus, these active oxygens such as .OH, $H_2O_2$, which are relative with serious diseases, are mostly caused by $O_2.^-$, and hence, it has been demanded to find a substance being capable of suppressing $O_2.^-$.

DISCLOSURE OF INVENTION

The present inventors have intensively studied the pharmacological activities of combination of the tetrazolylalkoxy-dihydrocarbostyril derivative (1) which is known to have an active oxygen suppressing activity with a known anti-hyperlipemic agent, Probucol, and have found that the combination exhibits excellent synergistic antioxidant activity as well as excellent synergistic activity for suppressing the superoxide which causes cerebral infarction, arteriosclerosis and renal diseases, and further exhibits significant improvement of insulin resistance and remarkably decreases the urinary excretion of glucose which is one of indexes for renal dysfunctions, and then have found that the combination of the tetrazolylalkoxy-dihydrocarbostyril derivative (1) and Probucol is effective for the prevention and/or treatment of cerebral infarction, arteriosclerosis, renal diseases (e.g. diabetic nephropathy, renal failure, nephritis), or diabetes owing to the excellent superoxide suppressing activity.

Thus, an object of the invention is to provide a combination drug for preventing and treating cerebral infarction comprising a tetrazolylalkoxy-dihydrocarbostyril derivative (1) and Probucol.

Another object of the invention is to provide a combination drug for preventing and treating arteriosclerosis comprising a tetrazolylalkoxy-dihydrocarbostyril derivative (1) and Probucol.

A further object of the invention is to provide a combination drug for preventing and treating renal diseases comprising a tetrazolylalkoxy-dihydrocarbostyril derivative (1) and Probucol.

A further object of the invention is to provide a combination drug for preventing and treating diabetes comprising a tetrazolylalkoxy-dihydrocarbostyril derivative (1) and Probucol.

A still further object of the invention is to provide an improved superoxide suppressant comprising a combination of a tetrazolylalkoxy-dihydrocarbostyril derivative (1) and Probucol.

DETAILED DESCRIPTION OF INVENTION

The carbostyril derivative to be inclusive as one of the component of the combination drug of the present invention is tetrazolylalkoxy-dihydrocarbostyril derivatives of the formula:

wherein R is a cycloalkyl group, A is a lower alkylene group, and the bond between 3- and 4-positions of the carbostyril nucleus means a single bond or a double bond, or a salt thereof.

In the above formula (1), the cycloalkyl group includes $C_3$-$C_8$ cycloalkyl groups such as cyclopropyl, cyclobutyl, cyclopentyl, cyclohexyl, cycloheptyl, and cyclooctyl. Preferred one is cyclohexyl. The lower alkylene group includes $C_1$-$C_6$ alkylene groups such as methylene, ethylene, propylene, tetramethylene, butyrene, and pentylene, among which preferred one is tetramethylene.

Preferable carbostyril derivative is 6-[4-(1-cyclohexyl-1H-tetrazol-5-yl)butoxy]-3,4-dihydrocarbostyril, which has been put on the market in the trade name of Cilostazol as an antiplatelet agent.

These carbostyril derivatives (1) and salts thereof and a process for preparation thereof are disclosed in U.S. Pat. No. 4,277,479. It is also disclosed in U.S. Pat. No. 6,743,806 that the carbostyril derivatives (1) have an active oxygen suppressing activity.

Another active ingredient, Probucol is a compound having a chemical name of 4,4'-isopropylidenedithiobis[2,6-di-tert-butylphenol], and has already been put on the market as an anti-hyperlipidemic agent. It is also known that this compound has an inhibitory activity of production of oxidized LDL (low-density lipoprotein) (cf. J. Clin. Invest., 77, p. 641, 1986)

These active ingredients, a carbostyril derivative (1) and Probucol may be administered together or separately, at the same time or different time. These ingredients may usually be used in a conventional pharmaceutical formulation. Then, these ingredients may be prepared in the pharmaceutical formulation in a single dosage form or in separate dosage forms.

The dosage forms are not specified but may be any conventional pharmaceutical formulations, for example, preparations for oral administration, such as tablets, capsules, granules, various liquid preparations suitable for oral administration, or preparations for parenteral administration, such as injections, suppositories.

The dose of these active ingredients is not limited to a specific range. The carbostyril derivatives (1) or a salt thereof may be used in an amount of 50 to 200 mg/day in adult (50 kg of body weight), which is administered once a day or by dividing into two to several times per day. Probucol may be used in an amount of 100 to 1000 mg/day in adult (50 kg of body weight), which may be administered at one time but may preferably be administered by dividing the daily dose into two to several times per day. When these ingredients are prepared in a single dosage form, they are incorporated in a ratio of 0.25 to 10 parts by weight of Probucol per 1 part by weight of the carbostyril derivative (1) or a salt thereof.

The preparations such as tablets, capsules, liquid for oral administration may be prepared by a conventional method. The tablets may be prepared by mixing the active ingredient(s) with conventional pharmaceutical carriers such as gelatin, starches, lactose, magnesium stearate, talc, gum arabic, and the like. The capsules may be prepared by mixing with inert pharmaceutical fillers or diluents and filled in a hard gelatin capsule or a soft capsule. The oral liquid preparations such as syrups or elixirs are prepared by mixing the active ingredient(s) and sweetening agents (e.g. sucrose), preservatives (e.g. methylparaben, propylparaben), colorants, flavors, and the like. The preparations for parenteral administration may also be prepared by a conventional method, for example, by dissolving the active ingredient(s) of the present invention in a sterilized aqueous carrier, preferably water or a saline solution. Preferred liquid preparation suitable for parenteral administration is prepared by dissolving the daily dose of the active ingredients as mentioned above in water and an organic solvent and further in a polyethylene glycol having a molecular weight of 300 to 5000, which is preferably incorporated with a lubricant such as sodium carboxymethylcellulose, methylcellulose, polyvinylpyrrolidone, and polyvinyl alcohol. The above liquid preparations may preferably be further incorporated with a disinfectant (e.g. benzyl alcohol, phenol, thimerosal), a fungicide, and further optionally with an isotonic agent (e.g. sucrose, sodium chloride), a topical anesthetic, a stabilizer, a buffer, and the like. In view of keeping stability, the preparation for parenteral administration may be filled in a capsule, followed by removing the aqueous medium by a conventional lyophilizing technique, and is recovered into a liquid preparation by dissolving in an aqueous medium when used.

According to the present invention, by combining the carbostyril derivative (1), particularly 6-[4-(1-cyclohexyl-1H-tetrazol-5-yl)butoxy]-3,4-dihydrocarbostyril, or a salt thereof with Probucol, they are effective on cerebral infarction, arteriosclerosis, renal diseases (e.g. diabetic nephropathy, renal failure, nephritis), or diabetes.

One of the mechanisms of exhibiting those effects may be owing to the excellent superoxide suppressing activity, that is they exhibit excellent synergistic antioxidant activity and synergistic superoxide suppressing effects, by which the superoxide affecting tissue cells are effectively removed. Besides, by suppressing superoxide, it results also in inhibition of production of .OH, $H_2O_2$, which are derived from the superoxide. The combination drug of the present invention can also inhibit the production of active oxygens such as $O_2.^-$, .OH, $H_2O_2$, which are the main cause of serious diseases. It is known that superoxide causes cerebral infarction (e.g. acute cerebral infarction, chronic cerebral infarction), arteriosclerosis, renal diseases (e.g. diabetic nephropathy, renal failure, nephritis) (cf. Antioxidants & Redox Signaling, 5, 2003, pp. 597-607, which discloses participation of $O_2.^-$ in cerebral infarction; Circ. Res., 86, 2000, pp. 494-501, which discloses that NAD(P)H oxidase produces $O_2.^-$ and participates in circulatory system diseases such as arteriosclerosis; Eur. J. Pharmacol., 450, 2002, pp. 67-76, which discloses participation of $O_2.^-$ in renal diseases).

Thus, by synergistic superoxide suppressant effects, the combination of the carbostyril derivative (1) and Probucol of the present invention can exhibit the desired effects for prevention and treatment of cerebral infarction, arteriosclerosis, renal diseases (e.g. diabetic nephropathy, renal failure, nephritis), or diabetes.

EXAMPLES

The present invention is illustrated by the following preparation examples and experiments of superoxide suppressing activity of the agent of the present invention, but should not be construed to be limited thereto.

Preparation 1

Preparation of Tablets:

| Components | Amount (g) |
| --- | --- |
| 6-[4-(1-Cyclohexyl-1H-tetrazol-5-yl)butoxy]-3,4-dihydrocarbostyril | 100 |
| Probucol | 250 |
| Lactose (Japanese Pharmacopeia) | 40 |
| Cornstarch (Japanese Pharmacopeia) | 40 |
| Crystalline cellulose (Japanese Pharmacopeia) | 20 |
| Hydroxypropylcellulose (Japanese Pharmacopeia) | 4 |
| Magnesium stearate (Japanese Pharmacopeia) | 2 |

The above active ingredients of the present invention, lactose, cornstarch and crystalline cellulose are mixed well and the mixture is granulated with 5% aqueous solution of hydroxypropylcellulose, and the granulated mixture is sieved with 200 mesh screen to dry the granules carefully, and then the granules are tabletted by a conventional method to give tablets (1000 tablets).

Pharmacological Experiments

Experiment 1

Synergistic Inhibition by Combination of Cilostazol and Probucol on NAD(P)H-dependent $O_2.^-$ production from Human Vascular Endothelial Cells (1) Materials and Methods:

Cell Cultures: HCAEC (Human coronary artery endothelial cells) were cultured in the endothelial cell basal media-2 (EGM-2) Bullet kit. Cells were grown to confluence at 37° C. in 5% $CO_2$ and used for experiments at not greater than passage 6.

Test materials were (1) Cilostazol alone (n=4), (2) Probucol alone (n=4), (3) a mixture of Cilostazol with Probucol (n=4): the final concentrations for Cilostazol were 0.3, 1.0, and 3.0 µM and Probucol 0.01, 0.03, and 0.1 µM, which were corresponding to the ratio of Cilostazol and Probucol between 3:1 and 300:1 by molecular weight.

(2) Measurement of Superoxide:

Cilostazol and Probucol were dissolved in dimethyl sulfoxide as 10 mM stock solutions. Immediately after the addition of Cilostazol and/or Probucol at the final concentrations of 0, 0.3, 1.0, 3.0 µM and 0, 0.01, 0.03, 0.1 µM, respectively, into the culture medium, TNF-α (50 ng/ml) was added and HCAEC were incubated for 4 hours. After cells were exposed to the TNF-α, endothelial homogenates were placed into the luminometer (Microlumat LB96P, EG & G Berthold). Immediately before recording chemiluminescence, NADH and NADPH (final concentration, 100 µM, each) were added, and dark-adapted lucigenin (bis-N-methylacridinium nitrate, 5 µM) was added via an autodispenser. Chemiluminescence intensity was recorded every 30 seconds for 15 minutes, and the respective background was subtracted. Chemiluminescence was expressed as counts per second per milligram of protein.

The statistical analysis was done in the following manner.

1) The effects in Cilostazol alone or Probucol alone were compared with the effects of their combination by Dunnett's test.

2) In order to evaluate the synergistic effects of their combination, two-way analysis of variance (two-way ANOVA) was carried out between the Control, Cilostazol alone, Probucol alone, and the combination.

All tests were done by two-sided test with significant level of 5%, by means of SAS Software (SAS Institute Japan, R8.1).

Figure 1:
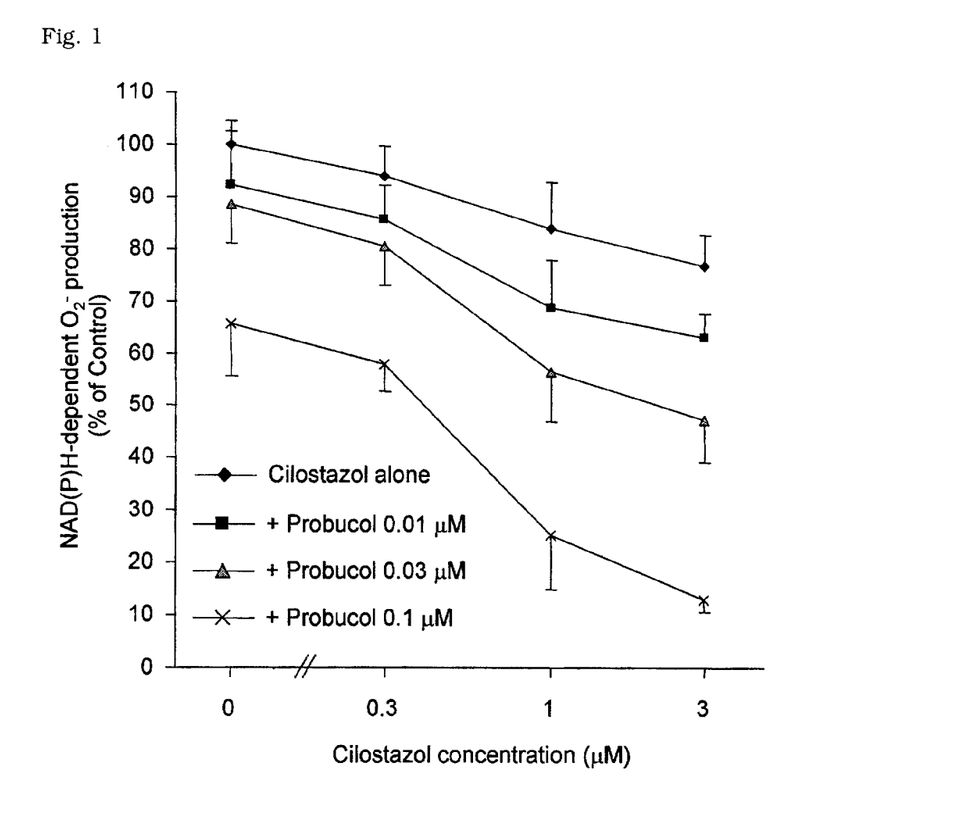
FIG. 1 is a graph showing correlation between Cilostazol concentration and NAD(P)H-dependent $O_2.^-$ production in inhibition by Cilostazol alone or a Combination of Cilostazol and Probucol on NAD(P)H-dependent $O_2.^-$ production.

(3) Results:

The results are shown in the accompanying FIG. 1. In FIG. 1, the longitudinal axis means NAD(P)H-dependent $O_2.^-$ production (% of Control), and the abscissa axis means Cilostazol concentration (µM), and the line with a rhombus mark means the data of Cilostazol alone, i.e. no Probucol (P0), the line with a square mark means the data of a mixture of Cilostazol with Probucol in an amount of 0.01 µM, the line with a triangle mark means the data of a mixture of Cilostazol with Probucol in an amount of 0.03 µM, and the line with an "x" mark means the data of a mixture of Cilostazol with Probucol in an amount of 0.1 µM.

As is seen from FIG. 1, when Cilostazol was used in combination with Probucol, the $O_2.^-$ production was significantly inhibited in comparison with Cilostazol alone. Furthermore, the suppressive effect was significantly potentiated by the combination of 3 µM Cilostazol and 0.1 µM Probucol (p=0.0322 by two-way ANOVA).

Experiment 2

Effects of Cilostazol and Probucol Alone and in Combination on Atherosclerosis in Low-Density Lipoprotein Receptor-Knockout Mice Fed High Cholesterol.

(1) Materials and Methods:

Low-density lipoprotein receptor-knockout (LDLR-KO) mice (J. Clin. Invest. 1993; 92: 883-893) (male, 9 weeks old, which was prepared by and kept in Otsuka Pharmaceutical Co, Ltd.) were used. The animals were treated by grouping in the following six groups.

1) Control group (n=13)
2) 0.3% Cilostazol-administered group (n=14)
3) 0.1% Probucol-administered group (n=14)
4) 0.5% Probucol-administered group (n=14)
5) 0.3% Cilostazol+0.1% Probucol administered group (n=14)
6) 0.3% Cilostazol+0.5% Probucol administered group (n=14)

Prior to start the experiment, the body weight of the animals and total cholesterol were measured, and based on both data, the animals were divided into six groups in random by stratified randomization method (SAS Software, R8.1). The doses of Probucol and Cilostazol were determined based on the reports (Horm. Metab. Res. 2001; 33: 472-479, and J. Pharmacol. Exp. Ther. 2005; 313: 502-509), respectively. In control group, mice were administered with a high-fat diet [i.e. a conventional feed (CRF-1, manufactured by Oriental Yeast Industries Co., LTD.) supplemented with cholesterol (1.25%), sodium cholate (0.5%) and cacao butter (15%)] and in the test material-administered group, the mice were administered with the high-fat diet combined with Cilostazol (0.3%) and/or Probucol (0.1% or 0.5%). The high-fat diet was administered to the LDLR-KO mice (since 9 weeks old) in order to induce atherosclerosis (in control group). In the test material-administration groups, the high-fat diet mixed with test material was administered to the mice (since 9 weeks old). The mice in both groups were dissected at eighth weeks after starting the administration of the diet. The atherosclerotic lesion was evaluated by picking up whole of the aorta under ether anesthesia, exposing the inner face of aorta and staining the fats with Sudan IV. The area of the atherosclerotic lesion (containing fats/lipids) in whole of the aorta was counted by image analysis of stained area and whole area of the aorta.

The statistical analysis was done in the following manner.

1) In order to confirm the synergistic effects of the combination of Cilostazol and Probucol, two-way ANOVA was carried out between the control group and the Cilostazol-administered group as well as between the Probucol-administered group and two agents-administered group, and thereby the interaction was observed.

2) The effects in Cilostazol- and Probucol-administered group were compared with the effects in control group by Dunnett's test. Moreover, the effects in Cilostazol- and Probucol-administered group were compared with the effects in Cilostazol+Probucol-administered group by Dunnett's test.

All tests were done by two-sided test with significant level of 5%, by means of SAS Software (SAS Institute Japan, R8.1).

(2) Results:

The area of atherosclerotic lesion was calculated as the ratio (%) of the area stained by Sudan IV to the area of whole aorta. The mean values±standard deviation were 10.1±4.7% in Control group, 6.6±2.6% in Cilostazol-administered group, 6.2±2.6% in 0.1% Probucol-administered group, 4.7±1.2% in 0.5% Probucol-administered group, 3.8±1.2% in Cilostazol+0.1% Probucol-administered group, and 2.9±1.5% in Cilostazol+0.5% Probucol-administered group.

Figure 2:
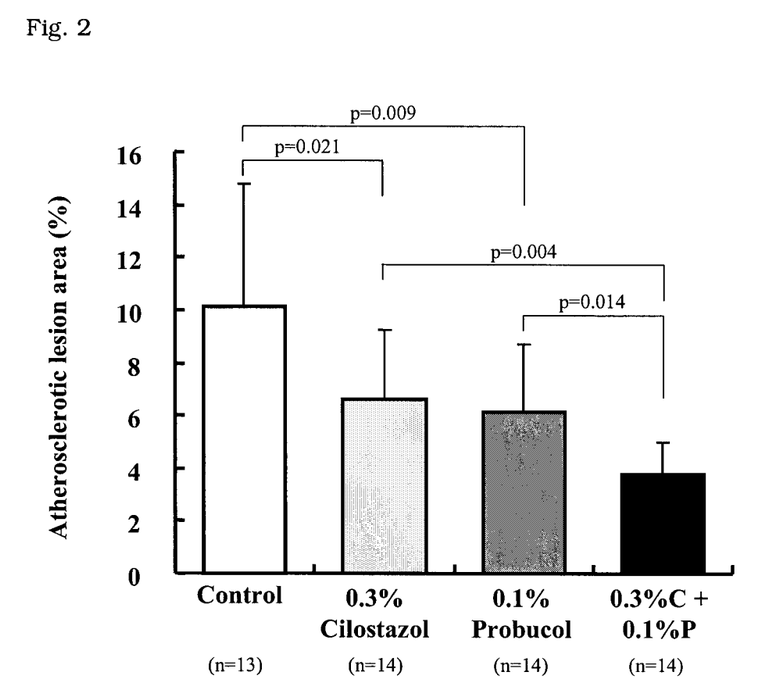
FIG. 2 is a graph showing inhibitory effects of 0.3% Cilostazol alone, 0.1% Probucol alone or a combination of 0.3% Cilostazol and 0.1% Probucol on atherosclerotic lesion in low-density lipoprotein receptor-knockout mice fed high cholesterol.
Figure 3:
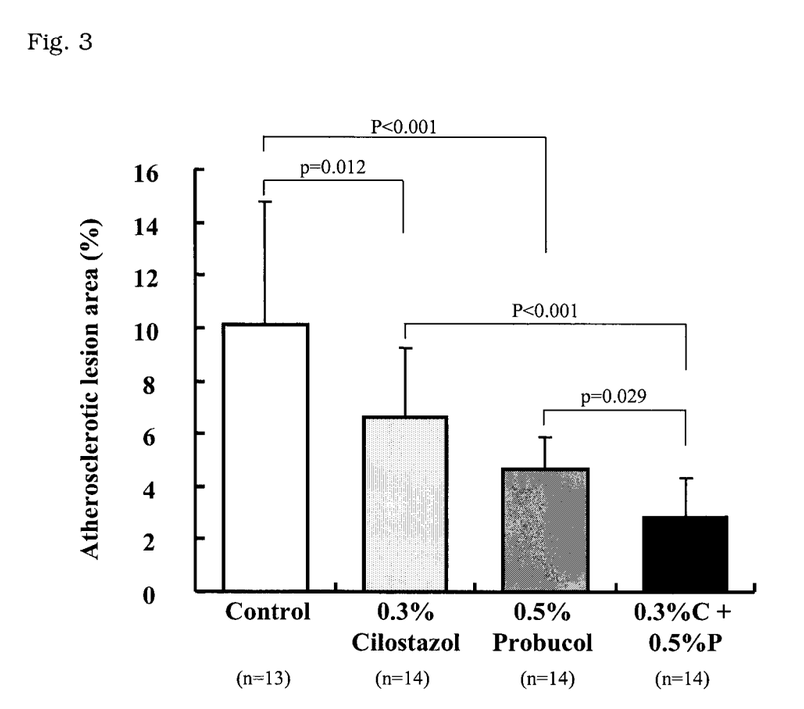
FIG. 3 is a graph showing inhibitory effects of 0.3% Cilostazol alone, 0.5% Probucol alone or a combination of 0.3% Cilostazol and 0.5% Probucol on atherosclerotic lesion in low-density lipoprotein receptor-knockout mice fed high cholesterol.

As shown in the accompanying FIG. 2 and FIG. 3, Cilostazol (0.3%) and Probucol (0.1 and 0.5%) inhibited the atherosclerotic lesion significantly in LDLR-KO mice. Besides, when combinations of two agents were administered, the arteriosclerosis was more potently inhibited in each combination with the doses of Probucol.

Experiment 3

Effects of Probucol and Cilostazol Alone and in Combination Against Focal Cerebral Ischemic Injury in Rats (1) Materials and Methods Male Sprague-Dawley rats weighing 280-320 g were anesthetized with pentobarbital sodium (20 mg/kg, i.p.), and placed on a heating pad (Homeothermic Blanket System, Harvard Apparatus, South Natick, Mass.) to maintain a constant rectal temperature (37±0.5° C.). Systemic arterial blood pressure, arterial blood gas and pH were measured before, during ischemia and after 22-h reperfusion.

Focal cerebral ischemia was induced by transient occlusion of the left middle cerebral artery (MCA) as previously described (Stroke 1989; 20:84-91). Surgical nylon suture thread (3-0 in size) with the round tip was advanced from the external carotid artery into the lumen of the internal carotid artery until blocking the flow of the MCA. Two hours after MCA occlusion, reperfusion was allowed by withdrawal of the suture thread until the tip cleared the internal carotid artery.

For analysis of cerebral infarct, at 22-h of reperfusion after 2-h left MCA occlusion, rats were given an overdose of thiopental sodium and decapitated, and then the brain was quickly removed and frozen by suspension over liquid nitrogen. The brain was cut into a 2-mm-thick coronal block. The brain slices were immersed in a 2% solution of 2,3,5-triphenyltetrazolium chloride (TTC) in normal saline at 37° C. for 30 min and then fixed in 10% phosphate-buffered formalin at 4° C. The TTC-stained brain slices were photographed using CCD video camera and the size of an infarct was calculated with image analysis system (Image-Pro Plus, Media Cybernetics, Maryland) and expressed as the percentage of infarcted tissue in reference to the ipsilateral hemisphere.

Cilostazol and probucol were dissolved in dimethyl sulfoxide (DMSO) as a 30 mg/ml stock solution and diluted to 10 mg/ml with phosphate buffered saline, respectively. In one group, rats orally received 20 mg/kg of cilostazol two times at 5 min, and 4 h after the completion of MCA occlusion, respectively. The other group of rats received 30 mg/kg probucol orally two times at 5 min, and 4 h after the completion of MCA occlusion, respectively. The combination group rats were treated with 20 mg/kg cilostazol plus 30 mg/kg probucol orally two times, respectively. Vehicle group received 30% DMSO solution (300 µl) orally without cilostazol/probucol.

The statistical analysis was done in the following manner. Data were expressed as mean±S.E.M. The comparison of the results of hemispheric infarct areas between groups is analyzed by repeated measures analysis of variance followed by Tukey's multiple comparison tests as a post hoc comparison. The differences were considered statistically significant at $P<0.05$.

(2) Results

Figure 4:
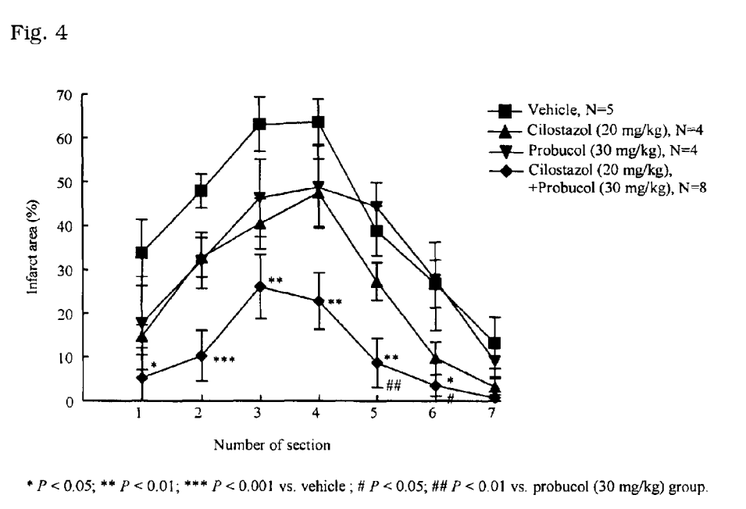
FIG. 4 is a graph showing effects of Probucol and Cilostazol alone and a combination of Probucol and Cilostazol against focal cerebral ischemic injury in rats.

The cerebral ischemic zone was consistently identified in the cortex and striatum of the left cerebral hemisphere as a distinct pale-stained area in the rats subjected to 2-h ischemia/22-h reperfusion. As shown in the accompanying FIG. 4, the infarct area was marginally reduced when the animals orally received 20 mg/kg cilostazol two times at 5 min and 4 h after the completion of 2-h ischemia, whereas 30 mg/kg probucol was without effect. Treatment with cilostazol (20 mg/kg) and probucol (30 mg/kg) in combination significantly reduced the hemispheric cerebral infarct area when compared with that of vehicle, indicative of a potent synergistic effect of combination therapy.

Experiment 4

Effects of Probucol and Cilostazol Alone and in Combination Against Urinary Excretion of Glucose and Insulin Resistance in Rats (1) Materials and Methods Otsuka Long-Evans Tokushima Fatty (OLETF) male rats (6 week olds) were divided randomly into the following four groups depending on the body weights by stratified randomized method (using SAS Software, R8.1):

| i) | Control group: | n = 10 |
|---|---|---|
| ii) | 0.3% Cilostazol-administered group: | n = 10 |
| iii) | 0.5% Probucol-administered group | n = 10 |
| iv) | 0.3% Cirostazol + 0.5% Probucol-administ. group: | n = 9 |

Immediately after the randomized grouping, high-fat diet (commercially available feed (CRF-1, manufactured by Oriental Yeast Industries Co., LTD.) supplemented with cholesterol (1.25%), sodium cholate (0.5%) and cacao butter (15%)) was administered to the mice in each group in order to promote the onset of renal disease. In the test-material administered groups, the high-fat diet combined with the test material was administered to each mouse immediately after grouping.

In the eleventh week after initiation of feeding, the mice were bled from the tail vein without anesthetization, and the plasma glucose and insulin level in plasma were measured. Separately, the urine was taken, and the urinary glucose was measured. Glucose was measured by an enzymatic method using a commercially available kit for measuring glucose, and the insulin was measured by a commercially available ELISA kit.

The statistical analysis was done in the following manner.

1) In order to confirm the synergistic effects of the combination of Cilostazol and Probucol, two-way ANOVA was carried out between the control group and the Cilostazol-administered group as well as between the Probucol-administered group and two agents-administered group, and thereby the interaction was observed.

2) The effects in Cilostazol- and Probucol-administered group were compared with the effects in control group by Dunnett's test. Moreover, the effects in Cilostazol- and Probucol-administered group were compared with the effects in Cilostazol+Probucol-administered group by Dunnett's test.

All tests were done by two-sided test with significant level of 5%, by means of SAS Software (SAS Institute Japan, R8.1). The data were shown by mean±SD (n).

Figure 5:
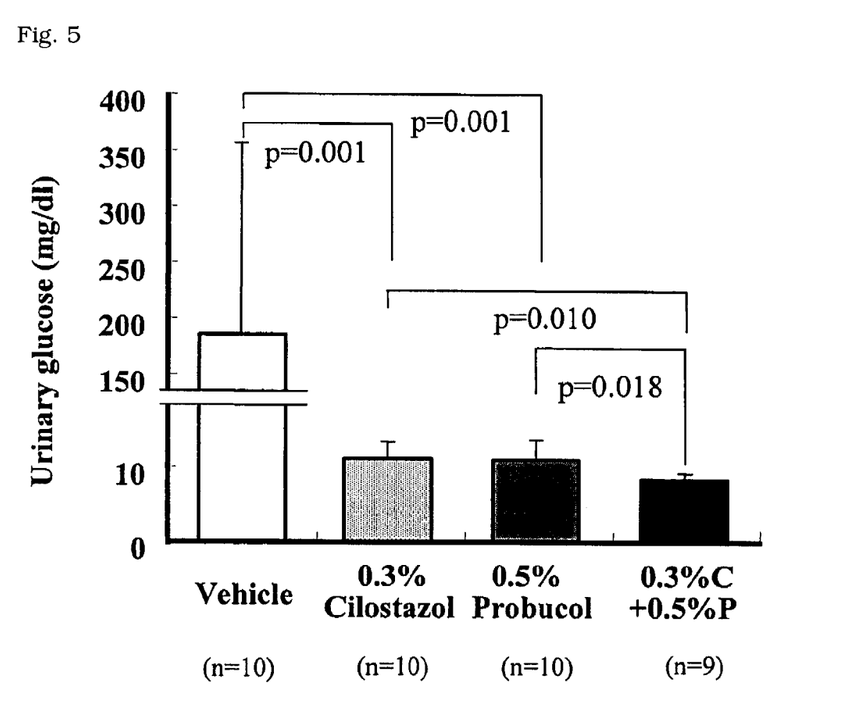
FIG. 5 is a graph showing effects of Probucol and Cilostazol alone and a combination of Probucol and Cilostazol against urinary excretion of glucose in rats.

(2) Results:

1) The effects of combination of two agents on urinary glucose:

The control group showed a urinary glucose level of 186±171 mg/dl (n=10) which was much higher than the data in normal rats (less than 10 mg/dl). In the groups administered with Cilostazol and Probucol each alone, the urinary glucose was significantly inhibited, each data being 11±2 mg/dl (n=10) and 11±3 mg/dl (n=10), respectively, but in the group administered with the combination of two agents, the urinary glucose was more significantly inhibited, as 8±1 mg/dl (n=9). These results are shown in the accompanying FIG. 5.

Figure 6:
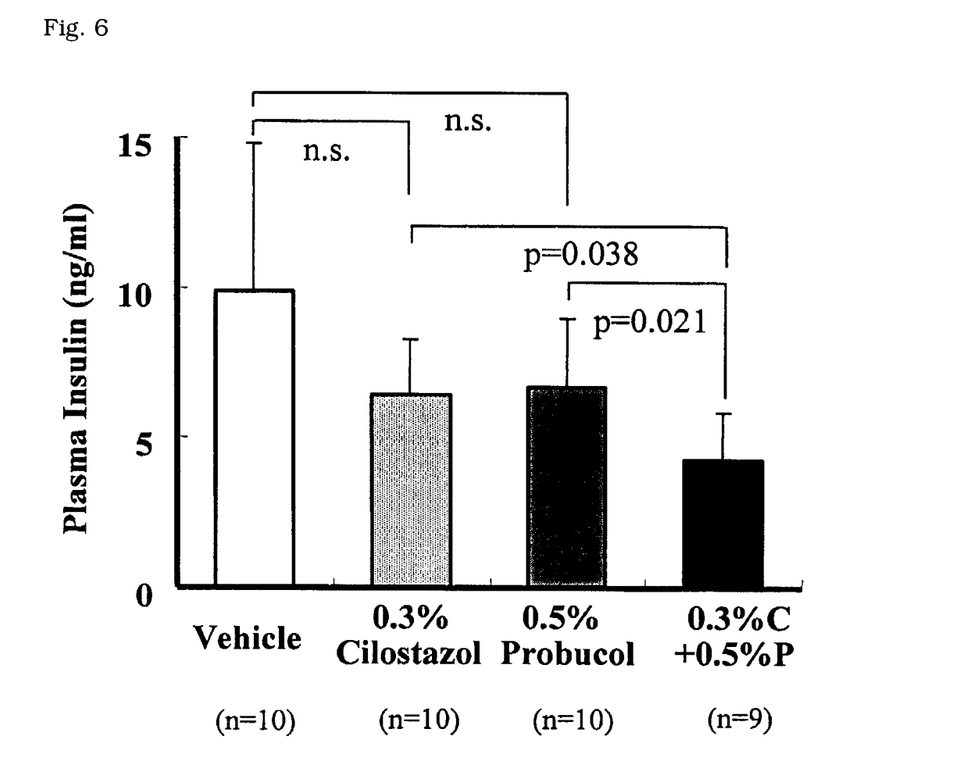
FIG. 6 is a graph showing effects of Probucol and Cilostazol alone and a combination of Probucol and Cilostazol against insulin resistance in rats.

2) The effects of combination of two agents on insulin resistance:

The control group showed a normal plasma glucose level of 162±16 mg/dl but showed a higher plasma insulin level of 9.9±5.0 ng/ml (n=10) in comparison with the data in normal rats. While neither Cilostazol nor Probucol showed any effect on the plasma glucose, the combination of Cilostazol and Probucol showed significantly inhibitory effects on the plasma insulin level compared with the administration of Cilostazol or Probucol alone. The results are shown in the accompanying FIG. 6.

Thus, the combination drug of Cilostazol and Probucol showed excellent improving effects on insulin resistance.

The invention claimed is:

1. A method for suppressing superoxide in a patient who has atherosclerosis, which comprises administering a combination of an effective amount of 6-[4-(1-cyclohexyl-1H-tetrazol-5-yl)butoxy]-3,4-dihydrocarbostyril or a salt thereof and an effective amount of Probucol to the patient.

* * * * *